(12) United States Patent
Gibson et al.

(10) Patent No.: US 10,067,060 B2
(45) Date of Patent: Sep. 4, 2018

(54) POLARIZATION SELECTIVE SURFACE ENHANCED RAMAN SPECTROSCOPY

(71) Applicant: Hewlett-Packard Development Company L.P., Houston, TX (US)

(72) Inventors: Gary Gibson, Palo Alto, CA (US); Huei Pei Kuo, Cupertino, CA (US); Steven J. Barcelo, Palo Alto, CA (US); Zhiyong Li, Foster City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 15/604,558

(22) Filed: May 24, 2017

(65) Prior Publication Data

US 2017/0254754 A1    Sep. 7, 2017

Related U.S. Application Data

(63) Continuation of application No. 14/763,510, filed as application No. PCT/US2013/023894 on Jan. 30, 2013, now Pat. No. 9,664,621.

(51) Int. Cl.
*G01J 3/44* (2006.01)
*G01N 21/65* (2006.01)
*G01N 21/21* (2006.01)

(52) U.S. Cl.
CPC .......... *G01N 21/658* (2013.01); *G01J 3/4412* (2013.01); *G01N 21/21* (2013.01)

(58) Field of Classification Search
CPC ......... G01J 3/4412; G01N 2201/06113; G01N 2201/0683

(Continued)

(56) References Cited

U.S. PATENT DOCUMENTS 3,807,862 A    4/1974  Hatzenbuhler
4,080,073 A    3/1978  Wolga
(Continued)

FOREIGN PATENT DOCUMENTS

CN    101806740    8/2010
CN    102311095    1/2012
(Continued)

OTHER PUBLICATIONS

"Polarization-dependent effects in surface-enhanced Raman scattering (SERS)" Physical Chemistry Chemical Physics P.G. Etchegoin et al.*
Etchegoin, Pablo G., et al. "Polarization-dependent effects in surface-enhanced Raman scattering (SERS)". Physical chemistry chemical physics, vol. 8, No. 22 (Jan. 1, 2006) pp. 2624-2628.*

(Continued)

*Primary Examiner* — Hina F Ayub
(74) *Attorney, Agent, or Firm* — HP Inc. Patent Department

(57) ABSTRACT

Polarization selective surface enhanced Raman spectroscopy (SERS) includes a plurality of nanofingers arranged as a SERS multimer to exhibit a polarization-dependent plasmonic mode and one or both of a stimulus source and a Raman detector. The stimulus source is to illuminate the SERS multimer with a stimulus signal and the Raman detector is to detect a Raman scattering signal emitted by an analyte in a vicinity of the SERS multimer. One or both of the Raman scattering signal has a polarization state dictated by or associated with the polarization-dependent plasmonic mode and the stimulus signal has a polarization state corresponding to the polarization-dependent plasmonic mode.

18 Claims, 3 Drawing Sheets

(58) Field of Classification Search
USPC .......................................................... 356/301
See application file for complete search history.

(56) References Cited

U.S. PATENT DOCUMENTS

| | | | |
|---|---|---|---|
| 5,541,413 | A | 7/1996 | Pearson et al. |
| 7,102,747 | B2 | 9/2006 | Wang et al. |
| 7,532,325 | B2 | 5/2009 | Ahmed et al. |
| 2006/0063188 | A1 | 3/2006 | Zanni et al. |
| 2008/0094621 | A1 | 4/2008 | Li et al. |
| 2011/0165586 | A1 | 7/2011 | Kim et al. |
| 2012/0029326 | A1 | 2/2012 | Kawamura et al. |
| 2012/0092660 | A1 | 4/2012 | Wu et al. |
| 2012/0107948 | A1 | 5/2012 | Li et al. |
| 2012/0127467 | A1 | 5/2012 | Ivanov et al. |
| 2012/0212732 | A1 | 8/2012 | Santori et al. |
| 2013/0003504 | A1 | 1/2013 | Caruso |

FOREIGN PATENT DOCUMENTS

| | | |
|---|---|---|
| EP | 1857810 | 11/2007 |
| EP | 2320216 | 5/2011 |
| JP | 2006-250655 | 9/2006 |
| JP | 2008-292425 | 12/2008 |
| JP | 2010-230352 | 10/2010 |
| JP | 2012-519833 | 8/2012 |
| JP | 2013-501228 | 1/2013 |
| WO | WO-2011/015412 | 2/2011 |
| WO | WO-2011/132355 | 10/2011 |
| WO | WO-2012/033097 | 3/2012 |
| WO | WO-2012128762 | 9/2012 |
| WO | WO-2012161683 | 11/2012 |

OTHER PUBLICATIONS

Fazio et al., "Re-radiation enchancement in polarization surface enhanced resonant Raman scattering of randomly oriented molecules on self-organized gold nanowires," ACS Nano 2011, V. 5, N. 7, pp. 5945-5956.*

Hartfield et al., "Development of a technique for separating Raman scattering signals from background emission with single-shot measurement potential," 33rd AIAA/ASME/SAE/ASEE Joint Propulsion Conf., Jul. 6-9, 1997, Seattle, WA, pp. 1-6.*

Wei et al., "Control light propagation and polarization with plasmons for surface enhanced Raman Scattering," Plasmonics: Nanoimaging, Nanofabrication, and their Applications V, ed. Satoshi Kawata et al., Proc. of SPIE vol. 7395, pp. 73950T-1-73950T-12.*

Wei, Hong, et al. "Polarization Dependence of Surface-Enhanced Raman Scattering in Gold Nanoparticle-Nanowire Systems", Nano Letters, vol. 8, No. 8 (Jan. 1, 2008), pp. 2497-2502.*

Alexander et al.,"A High-throughput Method for Controlled Hotspot Fabrication in SERS-active Gold Nanoparticle Dimer Arrays," J. Raman Spectroscopy, 2009, pp. 1-5.

International Search Report, dated Sep. 25, 2013, PCT Patent Application No. PCT/US2013/023894.

Luo et al.," Polarization-dependent surface enhanced Raman scattering from silver 1D nanoparticles arrays," J. Physical Chemistry Letters C, 2008, V. 112, pp. 11609-11613.

Supplementary European Search Report; dated Nov. 3, 2015; EP Patent Application No. 13873189.8; European Patent Office; Munich, DE; 3 pages.

Xu et al.,"Polarization-dependent surface enhanced Raman spectroscopy of isolated silver nanoaggregates," Chemphyschem, Communications, 2003, V. 4, pp. 1001-1005.

* cited by examiner

POLARIZATION SELECTIVE SURFACE ENHANCED RAMAN SPECTROSCOPY

CROSS-REFERENCE TO RELATED APPLICATIONS

This continuation application claims priority under 35 USC § 120 from co-pending U.S. patent application Ser. No. 14/763510 filed in Jul. 25, 2015 by Gibson et al. and entitled "POLARIZATION SELECTIVE SURFACE ENHANCED RAMAN SPECTROSCOPY," which was a national stage Application of and claiming priority to International Patent Application No. PCT/US2013/023894, filed on Jan. 30, 2013, and entitled "POLARIZATION SELECTIVE SURFACE ENHANCED RAMAN SPECTROSCOPY," the full disclosures each of which are hereby incorporated by reference.

STATEMENT REGARDING FEDERALLY SPONSORED RESEARCH OR DEVELOPMENT

N/A

BACKGROUND

Detection and identification (or at least classification) of unknown substances have long been of great interest and have taken on even greater significance in recent years. Among methodologies that hold particular promise for precision detection and identification are various forms of spectroscopy. Spectroscopy may be used to analyze, characterize and identify a substance or material using one or more of an absorption spectrum, a scattering spectrum and an emission spectrum that results when the material is illuminated by a form of electromagnetic radiation (e.g., visible light). The absorption, scattering and emission spectra produced by illuminating the material determine a spectral 'fingerprint' of the material. In general, the spectral fingerprint is characteristic of the particular material to facilitate identification of the material. Among the most powerful of optical emission spectroscopy techniques are those based on Raman scattering.

Scattering spectroscopy is an important means of identifying, monitoring and characterizing a variety of analyte species (i.e., analytes) ranging from relatively simple inorganic chemical compounds to complex biological molecules. Among the various types of scattering spectroscopy are methodologies that exploit Raman scattering and emission due to fluorescence (e.g., fluorescence emission) from an analyte. In general, scattering spectroscopy employs a signal (e.g., optical beam) to excite the analyte that, in turn, produces a response or scattered or emitted signal that is dependent on a characteristic (e.g., constituent elements or molecules of) the analyte. By detecting and analyzing the scattered or emitted signal (e.g., using spectral analysis), the analyte may be identified and even quantified, in some instances.

BRIEF DESCRIPTION OF THE DRAWINGS

Various features of examples in accordance with the principles described herein may be more readily understood with reference to the following detailed description taken in conjunction with the accompanying drawings, where like reference numerals designate like structural elements, and in which.

Figure 1:
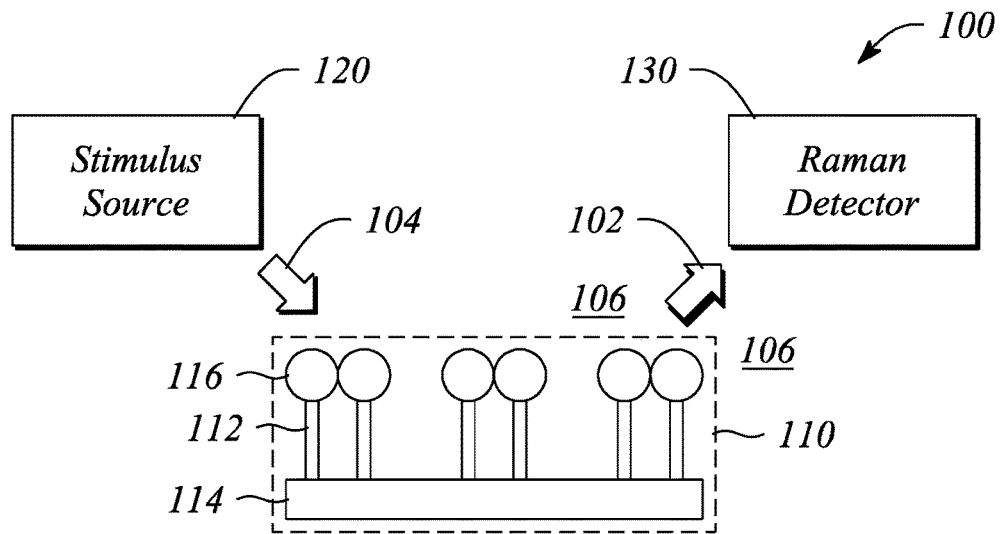
FIG. 1 illustrates a block diagram of a polarization selective surface enhanced Raman spectroscopy (SERS) system, according to an example consistent with the principles described herein.

Certain examples have other features that are one of in addition to and in lieu of the features illustrated in the above-referenced figures. These and other features are detailed below with reference to the above-referenced figures.

DETAILED DESCRIPTION

Examples in accordance with the principles described herein provide detecting or sensing of various analytes using scattering spectroscopy. In particular, examples in accordance with the principles described herein provide sensing of analytes by surface enhanced Raman spectroscopy. Moreover, the surface enhanced Raman spectroscopy sensing may provide discrimination between a Raman scattering signal and a background noise signal using polarization selectivity. For example, polarization selectivity may facilitate discriminating between the Raman scattering signal and various background noise signals including, but not limited to, a fluorescence background signal and stray ambient light.

According to various examples, Raman spectroscopy may employ a polarization-dependent plasmonic mode of or associated with a structure of a Raman-enhancing substrate (e.g., a dimer, trimer, etc.). Aligning a polarization of a stimulus signal and a polarization-dependent plasmonic mode may provide the polarization selectivity to discriminate between the Raman scattering signal and the background noise signal(s), in some examples. The polarization alignment may increase a coupling between the stimulus signal and the polarization-dependent plasmonic mode, for example. In other examples, polarization selectivity is provided by a Raman detector that is selectively matched to a polarization state of the Raman scattering signal. The Raman scattering signal polarization state may be determined or dictated by the polarization-dependent plasmonic mode, according to various examples. In yet other examples, both the stimulus signal polarization alignment and the selective matching of the Raman detector polarization with the Raman scattering signal are employed to discriminate between the Raman scattering signal and the background noise signal. According to various examples, the discrimination may improve, and in some examples significantly improve, a signal-to-noise ratio for the Raman scattering signal.

Examples of the principles described herein employ surface enhanced Raman spectroscopy (SERS) to detect or sense the presence of the analyte or a target species. Herein, other applicable forms of scattering spectroscopy that may be used include, but are not limited to, surface enhanced coherent anti-stokes Raman scattering (SECARS), resonant Raman spectroscopy, hyper Raman spectroscopy, various spatially offset and confocal versions of Raman spectroscopy, as well as direct monitoring of plasmonic resonances. SERS may provide detection and identification of the analyte and in some examples, quantification of the analyte. In particular, the detection or sensing may be provided for an analyte that is either adsorbed onto or closely associated with a surface in SERS, according to various examples. Herein, the scattering spectroscopy will generally be described with reference to SERS-based scattering spectroscopy for simplicity of discussion and not by way of specific limitation, unless otherwise indicated.

Raman-scattering optical spectroscopy or simply Raman spectroscopy, as referred to herein, employs a scattering spectrum or spectral components thereof produced by inelastic scattering of photons by an internal structure of a material being illuminated. These spectral components contained in a response signal (e.g., a Raman scattering signal) produced by the inelastic scattering may facilitate determination of the material characteristics of an analyte species including, but not limited to, identification of the analyte. Surface enhanced Raman spectroscopy (SERS) is a form of Raman spectroscopy that employs a 'Raman-active' or 'Raman-enhancing' surface. SERS may significantly enhance a signal level or intensity of the Raman scattering signal produced by a particular analyte species. In particular, in some instances, the Raman-enhancing surface includes a region associated with the tips of nanostructures such as, but not limited to, nanofingers or nanorods. The tips of the nanofingers may serve as nanoantennas to one or both of concentrate an illumination field and amplify a Raman emission leading to further enhancement of the strength of the Raman scattering signal, for example.

In some examples of SERS, a SERS surface that includes a plurality of nanofingers is configured to enhance production and emission of the Raman scattering signal from an analyte. Specifically, an electromagnetic field associated with and surrounding the nanofingers (e.g., tips of the nanofingers) in a 'Raman-enhancing' configuration may enhance Raman scattering from the analyte, in some examples. A relative location of the nanofingers themselves as well as tips of the nanofingers in the Raman-enhancing configuration may provide enhanced Raman scattering.

A 'nanorod' or equivalently a 'nanofinger' herein is defined as an elongated, nanoscale structure having a length (or height) that exceeds a nanoscale cross sectional dimension (e.g., width) taken in a plane perpendicular to the length, for example. In some examples, the length may exceed by several times the nanoscale cross sectional dimension. In particular, the length of the nanofinger is generally much greater than the nanofinger width (e.g., length is greater than about 2-3 times the width). In some examples, the length may exceed the cross sectional dimension (or width) by more than a factor of 5 or 10.

For example, the width may be about 40 nanometers (nm) and the height may be about 400 nm. In another example, the nanofinger width or diameter may be between about 100 nm and 200 nm and the length may exceed about 500 nm. For example, the width may be about 130-170 nm and the length may be about 500-800 nm. In yet another example, the width at a base of the nanofinger may range between about 20 nm and about 100 nm and the length may be more than about a 1 micrometer (μm). In another example, the nanofinger may be conical with a base having a width ranging from between about 100 nm and about 500 nm and a length that may range between about one half (0.5) μm and several micrometers.

In various examples, nanofingers of the plurality may be grown (i.e., produced by an additive process) or produced by etching or a subtractive process. For example, the nanofingers may be grown as nanowires using a vapor-liquid-solid (VLS) growth process. In other examples, nanowire growth may employ one of a vapor-solid (V-S) growth process and a solution growth process. In yet other examples, growth may be realized through directed or stimulated self-organization techniques such as, but not limited to, focused ion beam (FIB) deposition and laser-induced self assembly. In another example, the nanofingers may be produced by using an etching process such as, but not limited to, reactive ion etching, to remove surrounding material leaving behind the nanofingers. In yet other examples, various forms of imprint lithography including, but not limited to, nanoimprint lithography as well as various techniques used in the fabrication of micro-electromechanical systems (MEMS) and nano-electromechanical systems (NEMS) are applicable to the fabrication of the nanofingers and various other elements described herein.

A 'nanoparticle' herein is defined as a nanoscale structure having substantially similar dimensions of length, width and depth. For example, the shape of a nanoparticle may be a cylinder, a sphere, an ellipsoid, or a faceted sphere or ellipsoid, or a cube, an octahedron, a dodecahedron, or another polygon. The nanoparticle may be a substantially irregular three-dimensional shape, in other examples. The size of the nanoparticle may range from about 5 nm to about 300 nm, for example, in diameter or dimension. In some examples, the nanoparticle dimensions may be within a range of about 50 nm to about 100 nm, or about 25 nm to about 100 nm, or about 100 nm to about 200 nm, or about 10 nm to about 150 nm, or about 20 nm to about 200 nm.

In some examples, a nanoparticle may be a substantially homogeneous structure. For example, the nanoparticle may be a nanoscale metal particle (e.g., a nanoparticle of gold, silver, copper, etc.). In other examples, the nanoparticle may be a core-shell structure that is substantially inhomogeneous, by definition. For example, the nanoparticle may include a core of a first material that is coated by a second material that may be different from the first material. The second material of the coating or shell may be a metal while the first material may be either a conductor or a dielectric material. In another example, the second material may be a dielectric and the first material may be a conductor such as a metal, for example. A nanoparticle that is capable of supporting a plasmon (e.g., either a surface plasmon or a bulk plasmon) is defined as a 'plasmonic nanoparticle'. For example, a metal nanoparticle or a metal clad nanoparticle may serve as a plasmonic nanoparticle.

By definition herein, 'nanoscale' means a dimension that is generally less than about 1000 nanometers (nm). For example, a structure or particle that is about 5 nm to about 300 nm in extent is considered a nanoscale structure. Similarly, a slot having an opening size of between about 5 nm and 100 nm is also considered a nanoscale structure, for example.

Further, as used herein, the article 'a' is intended to have its ordinary meaning in the patent arts, namely 'one or more'. For example, 'a nanofinger' means one or more nanofingers and as such, 'the nanofinger' means 'the nanofinger(s)' herein. Also, any reference herein to 'top', 'bottom', 'upper', 'lower', 'up', 'down', 'front', 'back', 'left' or 'right' is not intended to be a limitation herein. Herein, the term 'about' when applied to a value generally means within the tolerance range of the equipment used to produce the value, or in some examples, means plus or minus 10%, or plus or minus 5%, or plus or minus 1%, unless otherwise expressly specified. Moreover, examples herein are intended to be illustrative only and are presented for discussion purposes and not by way of limitation.

Figure 2:
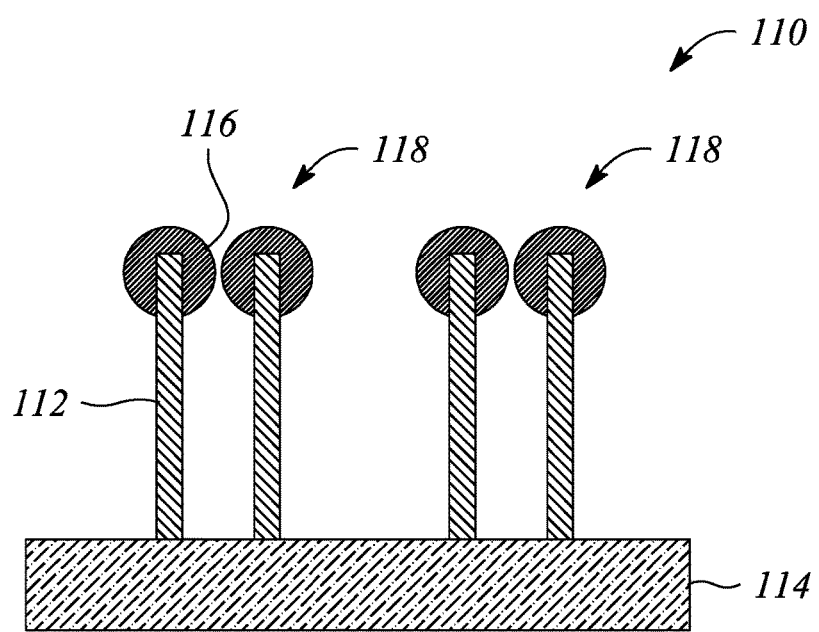
FIG. 2 illustrates cross sectional view of a portion of the SERS system illustrated in FIG. 1, according to an example consistent with the principles described herein.

FIG. 1 illustrates a block diagram of a polarization selective surface enhanced Raman spectroscopy (SERS) system 100, according to an example consistent with the principles described herein. FIG. 2 illustrates cross sectional view of a portion of the SERS system 100 illustrated in FIG. 1, according to an example consistent with the principles described herein. The SERS system 100 is configured to sense an analyte in a vicinity of the SERS system 100. For example, the analyte may be suspended in and carried by a fluid that flows through the SERS system 100, for example. The SERS system 100 senses the analyte by producing a Raman scattering signal 102 through an inelastic interaction between a stimulus signal 104 (e.g., optical beam) and the analyte, according to various examples.

As will be described in more detail below, the SERS system 100 may further discriminate between the Raman scattering signal 102 and a background noise signal 106, according to various examples. The background noise signal may be one or more of a fluorescence background signal and stray ambient light, for example. The SERS system 100 may discriminate between the Raman scattering signal 102 and the background noise signal 106 using a difference in polarization. In particular, the SERS system 100 may discriminate between a polarization state of the Raman scattering signal 102 and another state or different polarization state of the background noise signal. For example, the Raman scattering signal 102 may be linearly polarized and the background noise signal (e.g., fluorescence background noise) may be substantially unpolarized.

Referring to FIGS. 1 and 2, the polarization selective SERS system 100 includes a SERS sensing substrate 110. In particular, FIG. 1 illustrates a relationship between the SERS sensing substrate 110 and other elements of the polarization selective SERS system 100 while FIG. 2 illustrates the portion of the SERS system 100 that includes the SERS sensing substrate 110, in more detail. As illustrated, the stimulus signal 104 is depicted as an arrow pointing toward the SERS sensing substrate 110 and the Raman scattering signal 102 is depicted as an arrow pointing generally away from the SERS sensing substrate 110.

According to various examples, the SERS sensing substrate 110 includes a plurality of nanofingers 112. As illustrated in FIG. 2, the nanofingers 112 have a free end that is opposite to an end attached to a support 114. In some examples, the support 114 may include a substrate that provides support for the nanofingers 112. In some examples, the nanofingers 112 are rigidly attached to the support 114 at the fixed end. In other examples, the nanofingers 112 are indirectly attached to the support 114 through an intermediate material or layer, for example.

In various examples, the nanofinger 112 or a portion thereof may be configured to preferentially capture or retain the analyte in a vicinity of the nanofinger 112. For example, a surface of the nanofinger 112 may adsorb or bind the analyte. In some examples, the nanofingers 112 or a portion thereof may be functionalized to preferentially bind or provide selective adsorption of the analyte. In some examples, the nanofingers 112 may actively capture or trap the analyte (e.g., by a motion of the nanofingers 112).

According to some examples, the tips of the nanofingers 112 may either be substantially flattened or have a rounded (i.e., domed) shape. For example, the nanofinger 112 may have a tip that results naturally from a process (e.g., VLS growth) used to realize the nanofinger 112. In other examples, the nanofinger tip may be further processed to impart a particular shape to the free end of the nanofinger 112. The tips of the nanofingers 112 may be flattened using chemical-mechanical polishing, for example.

In some examples, the nanofinger 112 may include a semiconductor. For example, the semiconductor may be doped or undoped (i.e., substantially intrinsic) silicon (Si), germanium (Ge) or an alloy of Si and Ge. In other examples, the semiconductor may include one or more of gallium arsenide (GaAs), indium gallium arsenide (InGaAs), gallium nitride (GaN), or various other III-V, II-VI, and IV-VI compound semiconductors. In other examples, the nanofinger 112 may be or include a plastic or a polymer such as, but not limited to, polyurethane, poly(tert-butyl methacrylate) (P(tBMA)), polymethylmethacrylate (PMMA), polystyrene, polycarbonate or related plastics. In yet other examples, the nanofinger 112 may include a metal such as, but not limited to, gold, silver, platinum, other noble metals, aluminum copper, or an alloy or a combination of two or more metals.

According to some examples, the nanofinger 112 may include (e.g., be capped with) a nanoparticle 116 at the distal or free end of the nanofinger 112 (e.g., as illustrated in FIG. 2). The nanoparticle 116 may be attached to the nanofinger 112 in a vicinity of the tip, for example. In some examples, a material of the nanoparticle 116 may differ from a material of the nanofinger 112. For example, the nanofinger 112 may be a semiconductor or a polymer while the nanoparticle 116 may be a metal. In some of these examples, the nanoparticle 116 may be configured to one or both of enhance Raman scattering and facilitate selective analyte adsorption (e.g., through functionalization). In particular, in some examples, the nanoparticle 116 may include an electrically conductive material suitable for Raman enhancement. For example, the nanoparticle 116 may be or include a metal such as, but not limited to, gold, silver, platinum, other noble metals, aluminum, copper, as well as an alloy or a mixture of any of these metals with each other or another metal.

In some examples, the nanoparticles 116 may include substantially only the electrically conductive material. For example, the nanoparticles 116 may be metal nanoparticles 116. In other examples, the conductor (e.g., the metal) may be used to form a surface of the nanoparticles 116. For example, the nanoparticles 116 may include a metal shell surrounding a core of another material such as, but not limited to, a semiconductor or a dielectric.

According to various examples, the nanofingers 112 are Raman-enhancing structures. In particular, one or both of the entire nanofinger 112 and the nanoparticle 116 at the distal end may be Raman-enhancing. For example, a conductive surface (e.g., a metal surface) of the nanoparticles 116 may support a surface plasmon. In other examples, the nanoparticles 116 may support a bulk plasmon. Similarly, in various examples, the nanofinger 112 itself may support one or both of surface and bulk plasmons (e.g., when the nanofinger 112 is or includes an electrically conductive material such as metal). For example, the nanofinger 112 may include a metallic surface either along an entire length of the nanofinger 112 or in a vicinity of the tip at the free end. The presence of surface and bulk plasmons may be responsible for rendering one or both of the nanofinger 112 and the nanoparticle 116 Raman-enhancing, according to various examples.

According to various examples, the plurality of nanofingers 112 of the SERS sensing substrate 110 are arranged as an ordered group or 'multimer' that is referred to herein as a 'SERS multimer' 118. The SERS multimer 118 may include a group of two, three, four, five, six or more nanofingers 112, according to various examples. A SERS multimer 118 having two nanofingers 112 may be referred to as a 'dimer,' a SERS multimer 118 having three nanofingers 112 may be referred to as 'trimer,' a SERS multimer 118 having four nanofingers 112 may be referred to as a 'tetramer,' and so on. In some examples, the nanofingers 112 of the SERS multimer 118 may be arranged such that at least the free ends of the nanofingers 112 are located at vertices of a polygon (e.g., a digon, a trigon, a tetragon, a pentagon, a hexagon, and so on). The polygon may be a regular polygon, in some examples.

Figure 3A:
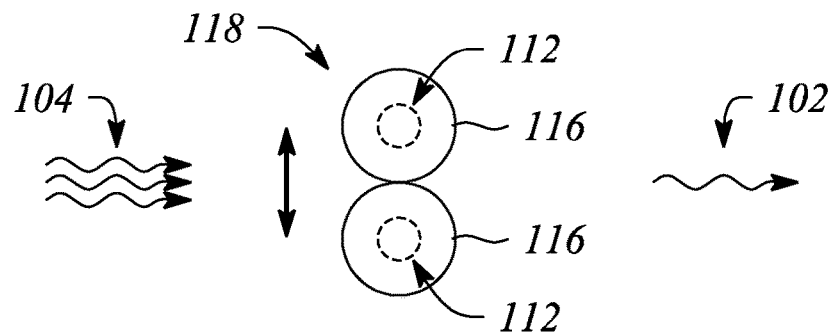
FIG. 3A illustrates top view of a SERS multimer having two nanofingers arranged as a dimer, according to an example consistent with the principles described herein.
Figure 3B:
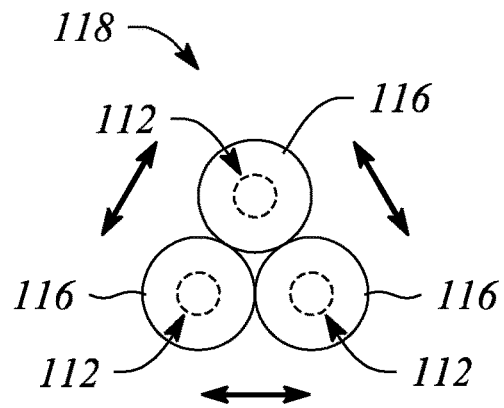
FIG. 3B illustrates top view of a SERS multimer having three nanofingers arranged as a trimer, according to an example consistent with the principles described herein.
Figure 3C:
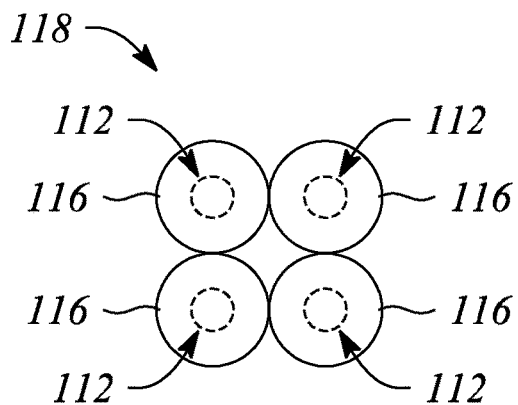
FIG. 3C illustrates top view of a SERS multimer having four nanofingers arranged as a tetramer, according to an example consistent with the principles described herein.

FIG. 3A illustrates a top view of a SERS multimer 118 having two nanofingers 112 arranged as a dimer, according to an example consistent with the principles described herein. FIG. 3B illustrates top view of a SERS multimer 118 having three nanofingers 112 arranged as a trimer, according to an example consistent with the principles described herein. FIG. 3C illustrates top view of a SERS multimer 118 having four nanofingers 112 arranged as a tetramer, according to an example consistent with the principles described herein.

According to various examples, the nanofingers 112 of the SERS multimer 118 may be either touching one another or spaced apart from one another. For example, either the tips of the nanofingers 112 themselves or the nanoparticles 116 on the tips of the nanofingers 112 in the SERS multimer 118 may be substantially touching or in close proximity, such that they are separated by a gap of about a few nanometers or less. Further, the nanofingers 112 in in the SERS multimer 118 may be tilted such that their tips lean toward one another. The tilting may facilitate contact between the tips or the nanoparticles 116 on the tips of the nanofingers 112, for example.

In some examples, the SERS sensing substrate 110 may include a plurality of SERS multimers 118. For example, the plurality of SERS multimers 118 may include several, tens, hundreds, or more SERS multimers 118. The SERS multimers 118 may be spaced apart from one another across the support substrate 114, for example. In other examples, the SERS multimers 118 may be immediately adjacent or even touching one another (e.g., a nanofinger 112 of a first SERS multimer 118 may touch a nanofinger 112 of an adjacent SERS multimer 118). A spacing between the SERS multimers 118 of the plurality when spaced apart may be either regular (i.e., a periodic spacing) or irregular (e.g., a substantially random spacing), according to various examples.

In particular, in some examples, the plurality of SERS multimers 118 may be arranged in a particular repeating ordered pattern or an 'array'. The array of SERS multimers 118, including both small arrays (e.g., bundles) and large arrays, may include, but is not limited to, a linear array or one-dimensional (1-D) array or a two-dimensional (2-D) array (e.g., a rectilinear array, a circular array, etc.). For example, a plurality of SERS multimers 118 may be arranged in a row for a 1-D array. A plurality of 1-D arrays or rows of SERS multimers 118 may be arranged next to one another to form a 2-D rectilinear array of SERS multimers 118, for example. Various other 2-D arrays may be employed in the polarization selective SERS system 100 including, but not limited to, polygonal arrays and circular arrays.

According to various examples, the SERS multimer 118 is configured to exhibit a polarization-dependent plasmonic mode, according to various examples. In particular, the arrangement of the nanofingers 112 as the SERS multimer 118 is configured to support a (i.e., as in 'one or more') particular or selected plasmonic mode. According to some examples, the particular plasmonic mode may be stimulated by the stimulus signal 104 (e.g., incident illumination signal) having a particular polarization state that is aligned to preferentially couple into the particular plasmonic mode of the SERS multimer 118. In turn, the particular plasmonic mode of the SERS multimer 118 may facilitate emission or scattering of the Raman scattering signal 102 having a particular polarization state that is also aligned with or dictated by the particular plasmonic mode of the SERS multimer 118, according to various examples. Herein, a 'polarization-dependent plasmonic mode' is defined as the aforementioned alignment of the particular plasmonic mode and the polarization state of one or both of the stimulus signal and the Raman scattering signal.

The polarization-dependent plasmonic mode of the SERS multimer 118 may be understood with reference to FIG. 3A, for example. As illustrated in FIG. 3A, the SERS multimer 118 is a dimer that includes a pair of nanofingers 112 and attached nanoparticles 116. The dimer has a long axis that passes through a center of each of the nanoparticles 116. The dimer configuration illustrated may support a dipole plasmonic mode oriented along the long axis of the dimer, according to some examples. A double-headed arrow in FIG. 3A illustrates an orientation of the dipole plasmonic mode (and long axis of the dimer), for example. FIG. 3B illustrates several double-headed arrows representing orientations of a plurality of possible example dipole plasmonic modes that may be associated with the SERS multimer 118 that is a trimer. Other dipole plasmonic modes beyond those illustrated in FIG. 3B are also possible, for example. Plasmonic modes having mode-orders higher than the dipole plasmonic mode are possible, especially in multimers that include more elements (e.g., nanofingers 112) than a dimer.

Considering the dimer illustrated in FIG. 3A by way of example and not limitation, an incident electromagnetic wave of the stimulus signal 104 may preferentially couple to and subsequently excite or stimulate the dipole plasmonic mode if an electric field vector of the incident electromagnetic wave is oriented substantially parallel with the long axis of the dimer. For example, an electromagnetic wave that is linearly polarized (i.e., linearly polarized light) has an electric field vector that describes or traces out a line perpendicular to a propagation direction of the electromagnetic wave. The line and its angle defined in a local coordinate system of the electromagnetic wave describe the polarization state of the electromagnetic wave. If the polarization state is aligned with the long axis of the dimer, the electric field of the electromagnetic wave may couple into and preferentially stimulate the dipole plasmonic mode.

In addition to being preferentially stimulated or excited, the polarization-dependent plasmonic mode of the SERS multimer 118 may also dictate a polarization state of a Raman scattering signal. For example, the dimer illustrated in FIG. 3A may support the dipole plasmonic mode, as described above. The dipole plasmonic mode, in turn, may produce a Raman scattering signal 102 through an interaction with an analyte. The Raman scattering signal 102 may have a polarization state that is substantially linear (i.e., linear polarization) as well as having an orientation (i.e., polarization angle) corresponding to an orientation of the long axis of the dimer. Similar polarization state dependence may be associated with or dictated by other polarization-dependent plasmonic modes present in the SERS multimer 118.

Referring again to FIG. 1, the polarization selective SERS system 100 further includes a stimulus source 120, as illustrated. The stimulus source 120 is configured to illuminate the SERS multimer 118 of the SERS sensing substrate 118 with the stimulus signal 104. In some examples, the stimulus signal 104 provided by the stimulus source 120 configured to illuminate the SERS multimer 118 is polarized to preferentially stimulate the polarization-dependent plasmonic mode of the SERS multimer 118. In particular, the stimulus signal 104 may be polarized according to a predetermined polarization state. The predetermined polarization state may be aligned to preferentially couple into the particular plasmonic mode of the SERS multimer 118.

In some examples, the stimulus source 120 may include a light source such as, but not limited to, a laser. The light source may be linearly polarized (i.e., have a linear polarization state), for example. The stimulus source 120 may further include a polarizer to rotate or otherwise adjust the polarization state of the stimulus source 120 to be aligned with the particular plasmonic mode of the SERS multimer 118, according to some examples. In some examples, the polarizer may have a selectable polarization state. The selectable polarization state may be configured to produce the stimulus signal 104 with a polarization state that corresponds with and preferentially excites the polarization-dependent plasmonic mode of the SERS multimer 118, according to various examples. For example, the polarizer may be a quarter-wave plate to convert a linear polarization of the stimulus signal 104 into a circular polarization. The polarizer may further include a linear polarizer having an adjustable or selectable polarization angle to produce a stimulus signal 104 having a linear polarization state that corresponds to the polarization angle, for example. Linear polarizers that may be employed include, but are not limited to, dichroic polarizers, a thin-film dielectric coating and related beam-splitting (e.g., birefringent crystal) polarizers, and wire grid or slit-polarizers, for example.

In some examples, the polarizer may provide a rotatable polarization. A half-wave plate may be used to rotate the polarization (e.g., of a linear polarized stimulus signal 104), for example. The rotatable polarization may provide a linear polarization state of the stimulus signal 104 that rotates through a plurality of polarization angles. In particular, the rotation of the linear polarization state may pass through or exhibit a first polarization state of the stimulus signal 104 that substantially corresponds to and for example, preferentially excites the polarization-dependent plasmonic mode of the SERS multimer 118 at a first time. At a second time, the linear polarization state may pass through or exhibit a second polarization state that is substantially orthogonal to the first polarization state. The second polarization state being orthogonal to the first polarization state may not correspond to and thus fail to excite the polarization-dependent plasmonic mode of the SERS multimer 118. A difference between the excitation of the polarization-dependent plasmonic mode at the first and second polarization states may facilitate discriminations between the Raman scattering signal that is related to the excitation of the polarization-dependent plasmonic mode and a background noise signal that is not substantially related to the polarization-dependent plasmonic mode excitation, according to some examples. A similar excitation difference using the first and second polarization states may be provided by the polarizer having selectable polarization states as opposed to a rotatable polarization, according to other examples.

As illustrated in FIG. 1, the polarization selective SERS system 100 further includes a Raman detector 130. The Raman detector 130 is configured to detect the Raman scattering signal 102 emitted by an analyte in a vicinity of the SERS multimer 118 of the SERS sensing substrate 110, according to various examples. The Raman scattering signal 102 has a polarization state associated with or dictated by the polarization-dependent plasmonic mode. In some examples, the Raman detector 130 is configured to to discriminate between the polarization state of the Raman scattering signal 102 and a differing polarization state of a background noise signal.

In some examples, the Raman detector 130 includes a polarization discriminator and a spectrometer. The spectrometer is configured to detect and measure a spectrum of the Raman scattering signal 102. The polarization discriminator is configured to selectively discriminate between various possible polarizations of a received signal including, but not limited to, the Raman scattering signal 102. In particular, the polarization discriminator is configured to provide polarization discrimination of a polarization state corresponding to a polarization state of the Raman scattering signal 102 dictated by the polarization-dependent plasmonic mode of the SERS multimer 118.

In some examples, the polarization discriminator is configured to provide a selectable polarization state. For example, the polarization discriminator may be configured to process (e.g., pass) a linear polarization state having a particular polarization angle. In some examples, the polarization discriminator is configured to process a rotatable polarization state. For example, the polarization discriminator may include a linear polarizer that rotates through a plurality of polarization states. In some examples, the polarization discriminator is configured to preferentially receive one or both of a primary component of the polarization state of the Raman scattering signal 102 and a component of the polarization state that is orthogonal to the primary component. For example, the polarization discriminator may preferentially process two orthogonal polarization states, one corresponding to the primary component and another corresponding to the component orthogonal to the primary component. A difference between the detection of the polarization-dependent plasmonic mode at the first and second polarization states may facilitate discriminations between the Raman scattering signal that is related to the emission of the polarization-dependent plasmonic mode and a background noise signal that is not substantially related to the polarization-dependent plasmonic mode excitation, according to some examples.

In some examples, the polarization discriminator includes or substantially shares the polarizer of the stimulus source 120. For example, the light source may produce the stimulus signal 104, which then passes through the polarizer. The Raman scattering signal 102 produced at the SERS multimer 118 may then pass through the polarizer, be separated from the stimulus signal 104 (e.g., by a beam splitter) and be directed to the spectrometer, for example.

Figure 4:
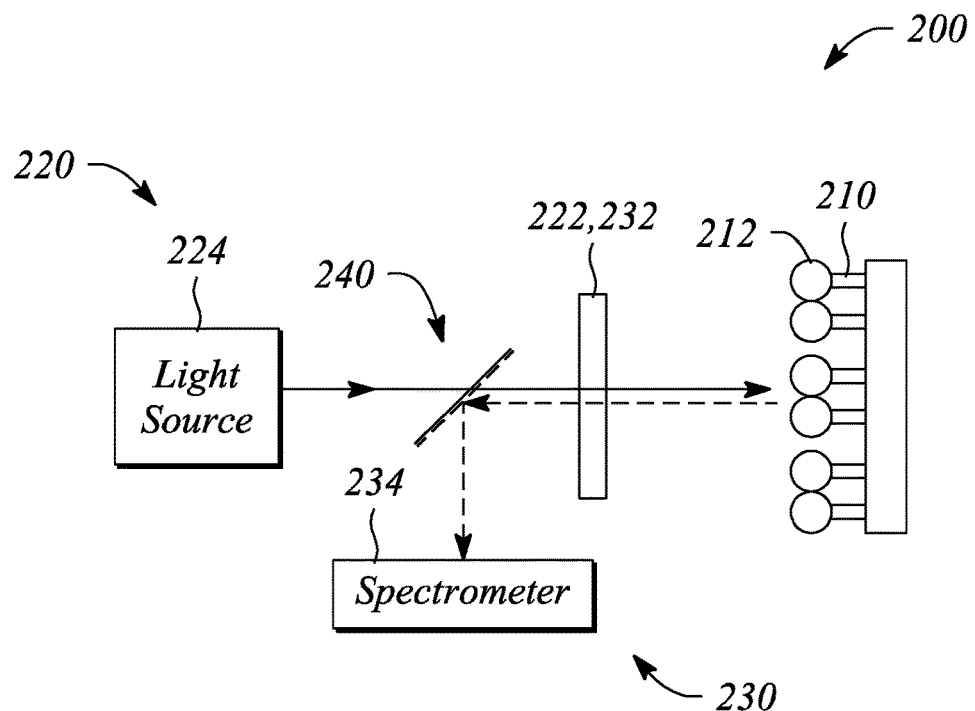
FIG. 4 illustrates a block diagram of a polarization selective surface enhanced Raman spectroscopy (SERS) system, according to an example consistent with the principles described herein.

FIG. 4 illustrates a block diagram of a polarization selective surface enhanced Raman spectroscopy (SERS) system 200, according to an example consistent with the principles described herein. As illustrated, the polarization selective SERS system 200 includes a plurality of nanofingers 210 arranged as a multimer. According to various examples, each nanofinger 210 includes a SERS-enhancing nanoparticle 212 at a free end. The multimer is configured to exhibit a polarization-dependent plasmonic mode. In some examples, the nanofinger 210 and the SERS-enhancing nanoparticle 212 are substantially similar to the nanofinger 112 and the nanoparticle 116 described above with respect the polarization selective SERS system 100. In addition, in some examples, the multimer is substantially similar to the SERS multimer 118 described above with respect to the polarization selective SERS system 100.

As illustrated, the polarization selective SERS system 200 further includes one or both of a stimulus source 220 that includes a polarizer 222 and a Raman detector 230 that includes a polarization discriminator 232. According to various examples, the stimulus source 220 that includes the polarizer 222 is configured to produce a stimulus signal with a controllable polarization state. The stimulus signal with the controllable polarization state is configured, in turn, to illuminate the multimer with a polarization state corresponding to the polarization-dependent plasmonic mode of the multimer. The Raman detector 230 that includes the polarization discriminator 232 is configured to detect a Raman scattering signal emitted by an analyte in a vicinity of the multimer, according to various examples. In particular, the Raman detector 230 is configured to preferentially receive a polarization state of the Raman scattering signal and to reject or substantially reject a background noise signal having a different polarization state from that of the Raman scattering signal.

In some examples, the stimulus source 220 is substantially similar to the stimulus source 120 described above with respect to the polarization selective SERS system 100. In particular, the stimulus source 220 may further include a light source 224 (e.g., a laser) to generate the stimulus signal. In some examples, the Raman detector 230 is substantially similar to the Raman detector 130 described above with respect to the polarization selective SERS system 100. In particular, the Raman detector 230 may further include a spectrometer 234 or another apparatus to detect and measure the Raman scattering signal.

In some examples, one or both of the stimulus source polarizer 222 and the polarization discriminator 232 may include a rotatable polarizer. In some examples, the rotatable polarizer is shared by both the stimulus source 220 and the Raman detector 230. For example, the rotatable polarizer may be positioned to intercept and polarize both the stimulus signal and the Raman scattering signal to serve as both the polarizer 222 and the polarization discriminator 232, as illustrated in FIG. 4. The system 200 may further include a beam splitter 240 configured to separate the stimulus signal and the Raman scattering signal and further, to direct the Raman scattering signal to the spectrometer 234, as is further illustrated in FIG. 4. In another example (not illustrated), the polarizer 222 may be located between the light source 224 and the beam splitter 240, while the polarization discriminator 232 is located between the beam splitter 240 and the spectrometer 234. In this configuration, polarization of the stimulus signal and polarization discrimination may be independently controlled. Other configurations including not using the beam splitter 240 are also possible, according to other examples.

In some examples, the multimer may be a dimer configured to exhibit the polarization-dependent plasmonic mode substantially aligned with a long axis of the dimer. In some examples, the background noise signal may be a substantially unpolarized fluorescence signal. In some examples, the background noise signal may be stray ambient light. In yet other examples, the background noise signal may be a combination of the fluorescence signal and stray ambient light.

Figure 5:
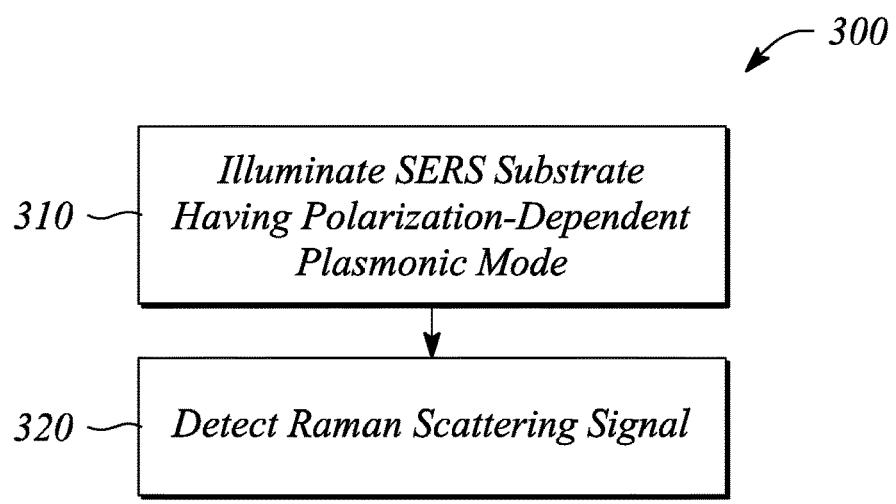
FIG. 5 illustrates a flow chart of a method of polarization selective surface enhanced Raman spectroscopy (SERS), according to an example consistent with the principles described herein.

FIG. 5 illustrates a flow chart of a method 300 of polarization selective surface enhanced Raman spectroscopy (SERS), according to an example consistent with the principles described herein. As illustrated, the method 300 of polarization selective SERS includes illuminating 310 a SERS substrate with a stimulus signal. According to various examples, the SERS substrate includes a plurality of nanofingers arranged as a multimer. Each nanofinger may include a SERS-enhancing nanoparticle at a free end of the nanofinger. The free end may be substantially opposite an end of the nanofinger attached to a support, for example.

In various examples, the illuminated multimer is configured to exhibit a polarization-dependent plasmonic mode. In some examples, illuminating 310 the SERS substrate includes emitting a polarized stimulus signal or a stimulus signal having a particular polarization state. For example, the particular polarization state may be a polarization state that is aligned with the multimer. Illuminating 310 the SERS substrate with a polarized stimulus signal may be employed to preferentially couple to or preferentially stimulate (e.g., excite) the polarization-dependent plasmonic mode of the multimer. When the multimer is a dimer, the polarization state of the stimulus signal may be a linear polarization state having a predetermined polarization angle corresponding to an orientation of a long axis of the dimer, for example.

In some examples, the SERS substrate may be substantially similar to the SERS sensing substrate 110 described above with respect to the polarization selective SERS system 100. In particular, the nanofingers and SERS-enhancing nanoparticles may be substantially similar to respective ones of the nanofingers 112 and the nanoparticles 116 of the SERS sensing substrate 110, as described above. Similarly, the illuminated multimer may be substantially similar to the SERS multimer 118 described above with respect to the polarization selective SERS system 100, in some examples.

The method 300 of polarization selective SERS further includes detecting 320 a Raman scattering signal emitted by an analyte in a vicinity of the multimer. In some examples, detecting 320 the Raman scattering signal selectively discriminates between a polarization state of the Raman scattering signal associated with or dictated by the polarization-dependent plasmonic mode of the multimer and a background noise signal having a different polarization state. In some examples, detecting 320 the Raman scattering signal may be performed using a detector that is substantially similar to the Raman detector 130 described above with respect to the polarization selective SERS system 100. In particular, detecting 320 the Raman scattering signal may employ polarization discrimination provided by, for example, a polarization discriminator that is substantially similar to the polarization discriminator, described above. In some examples, polarization is employed in both illuminating 310 the SERS substrate and detecting 320 the Raman scattering signal in that both the emitted stimulus signal is polarized and detecting 320 selectively discriminates between the polarization states.

In some examples, the method 300 of polarization selective SERS further includes rotating one or both of a polarization state of the stimulus signal and a polarization state of a polarization discriminator used to selectably discriminate the Raman scattering signal polarization state. In some examples, detecting 320 the Raman scattering signal includes detecting both of a principal or primary component of the Raman scattering signal polarization state and a component that is substantially orthogonal to the primary component. A difference between the principal component and the orthogonal component may be used to selectably detect the Raman scattering signal, for example.

Thus, there have been described examples of a polarization selective SERS system and a method of polarization selective SERS that employ a polarization-dependent plasmonic mode of a SERS multimer. It should be understood that the above-described examples are merely illustrative of some of the many specific examples that represent the principles described herein. Clearly, those skilled in the art can readily devise numerous other arrangements without departing from the scope as defined by the following claims.

What is claimed is:

1. A polarization selective surface enhanced Raman spectroscopy (SERS) system comprising:
   a SERS sensing substrate comprising a plurality of nanofingers arranged as a SERS multimer to exhibit a polarization-dependent plasmonic mode;
   a stimulus source to selectively illuminate the SERS multimer with a first stimulus signal having a first polarization to stimulate the polarization-dependent plasmonic mode of the SERS multimer, and a second stimulus signal having a second polarization substantially orthogonal to the first polarization; and
   a Raman detector to detect a Raman scattering signal emitted by an analyte in a vicinity of the SERS multimer, the Raman scattering signal having a polarization state associated with the polarization-dependent plasmonic mode,
   wherein the Raman detector is to measure a first spectrum in response to the first stimulus signal, a second spectrum in response to the second stimulus signal, and to discriminate between the Raman scattering signal and a background noise signal based on a difference between the first and second measured spectra.

2. The polarization selective SERS system of claim 1, wherein the nanofingers of the SERS multimer comprise a SERS-enhancing nanoparticle at a free end of the nanofingers opposite an end that is attached to a supporting surface of the SERS sensing substrate.

3. The polarization selective SERS system of claim 2, wherein the nanoparticle comprises a metal surface that is functionalized to adsorb the analyte.

4. The polarization selective SERS system of claim 1, wherein the SERS multimer is a dimer, both of the polarization-dependent plasmonic mode and the Raman scattering signal polarization state being substantially aligned with a long axis of the dimer.

5. The polarization selective SERS system of claim 1, wherein the background noise signal comprises one or both of a fluorescence background signal and stray ambient light.

6. The polarization selective SERS system of claim 1, wherein the stimulus source comprises a polarizer having a selectable polarization state to produce the stimulus signal with a polarization state that corresponds with and excites the polarization-dependent plasmonic mode of the SERS multimer.

7. The polarization selective SERS system of claim 1, wherein the detector comprises a polarization discriminator to receive one or both of a primary component of the polarization state of the Raman scattering signal and a component of the polarization state that is orthogonal to the primary component.

8. The polarization selective SERS system of claim 1, wherein each of the nano fingers comprises a spherical metal tip and wherein the multimer comprises:
   a first pair of the nano fingers having a first long axis passing through a center of the tip of the first pair of nano fingers, the first long axis providing a first one of the plurality of polarization-dependent plasmonic modes;
   a second pair of the nano fingers having a second long axis passing through a center of the tip of the second pair of nano fingers, the second long axis providing a second one of the plurality of polarization-dependent plasmonic modes,
   wherein the stimulus signal is to illuminate the multimer with a polarization state preferentially corresponding to the first one of the polarization-dependent plasmonic modes as compared to the second one of the polarization-dependent plasmonic modes, and
   wherein the polarization discriminator is to receive a polarization state of the Raman scattering signal corresponding to the first one of the polarization-dependent plasmonic modes as compared to a polarization state of the Raman scattering signal corresponding to the second one of the polarization-dependent plasmonic modes.

9. A polarization selective surface enhanced Raman spectroscopy (SERS) system comprising:
   a plurality of nanofingers arranged as a multimer, the nanofingers comprising a SERS-enhancing nanoparticle at a free end, the multimer to exhibit a polarization-dependent plasmonic mode;
   a stimulus source comprising a polarizer to produce a stimulus signal with a controllable polarization state, wherein the stimulus source is through the first stimulus signal to illuminate the multimer with a polarization state corresponding to the polarization-dependent plasmonic mode and a second stimulus signal having a second polarization substantially orthogonal to the first polarization; and
   a Raman detector to detect a first excitation signal in response to the first stimulus signal and a second excitation signal in response to the second stimulus signal, the first and second stimulus signals comprising a Raman scattering signal emitted by an analyte in a vicinity of the multimer, the Raman detector comprising a polarization discriminator to discriminate between the Raman scattering signal a background noise signal based on a difference between the first and second detected excitation signals.

10. The polarization selective SERS system of claim 9, wherein one or both of the stimulus source polarizer and the polarization discriminator comprises a rotatable polarizer.

11. The polarization selective SERS system of claim 10, wherein the rotatable polarizer is shared by both the stimulus source and the Raman detector.

12. The polarization selective SERS system of claim 9, wherein the multimer is a dimer to exhibit the polarization-dependent plasmonic mode substantially aligned with a long axis of the dimer.

13. The polarization selective SERS system of claim 9, wherein the background noise signal comprises a substantially unpolarized fluorescence signal.

14. The polarization selective SERS system of claim 9, wherein each of the nano fingers comprises a spherical metal tip and wherein the multimer comprises:
   a first pair of the nano fingers having first long axis passing through a center of the tip of the first pair of nano fingers, the first long axis providing a first one of the plurality of polarization-dependent plasmonic modes;

a second pair of the nano fingers having a second long axis passing through a center of the tip of the second pair of nano fingers, the second long axis providing a second one of the plurality of polarization-dependent plasmonic modes, wherein the stimulus signal is to illuminate the multimer with a polarization state corresponding to the first one of the polarization-dependent plasmonic modes as compared to the second one of the polarization-dependent plasmonic modes.

15. A method of polarization selective surface enhanced Raman spectroscopy (SERS), the method comprising:
illuminating a SERS substrate with a first stimulus signal having a first polarization to stimulate the polarization-dependent plasmonic mode of the SERS multimer, and a second stimulus signal having a second polarization substantially orthogonal to the first polarization, the SERS substrate comprising a plurality of nanofingers arranged as a multimer, the nanofingers comprising a SERS-enhancing nanoparticle at a free end opposite an end of the nanofinger attached to a support, the illuminated multimer to exhibit a polarization-dependent plasmonic mode;
detecting a first excitation signal in response to the first stimulus signal and a second excitation signal in response to the second stimulus signal, the first and second stimulus signals comprising a Raman scattering signal emitted by an analyte in a vicinity of the multimer; and
discriminating between the Raman scattering signal and a background noise signal based on a difference between the first and second detected excitation signals.

16. The method of polarization selective SERS of claim 15, further comprising rotating one or both of a polarization state of the stimulus signal and a polarization of a polarization discriminator used to selectably discriminate the Raman scattering signal polarization state.

17. The method of polarization selective SERS of claim 15, wherein the background noise signal comprises a substantially unpolarized fluorescence signal.

18. The method of claim 15, wherein each of the nano fingers comprises a spherical metal tip and wherein the multimer comprises:
a first pair of the nano fingers having first long axis passing through a center of the tip of the first pair of nano fingers, the first long axis providing a first one of the plurality of polarization-dependent plasmonic modes;
a second pair of the nano fingers having a second long axis passing through a center of the tip of the second pair of nano fingers, the second long axis providing a second one of the plurality of polarization-dependent plasmonic modes,
wherein the stimulus signal is to illuminate the multimer with a polarization state preferentially corresponding to the first one of the polarization-dependent plasmonic modes as compared to the second one of the polarization-dependent plasmonic modes, and
wherein the polarization discriminator is to receive a polarization state of the Raman scattering signal corresponding to the first one of the polarization-dependent plasmonic modes as compared to a polarization state of the Raman scattering signal corresponding to the second one of the polarization-dependent plasmonic modes.

* * * * *

UNITED STATES PATENT AND TRADEMARK OFFICE
CERTIFICATE OF CORRECTION

PATENT NO. : 10,067,060 B2
APPLICATION NO. : 15/604558
DATED : September 4, 2018
INVENTOR(S) : Gary Gibson et al.

Page 1 of 1

It is certified that error appears in the above-identified patent and that said Letters Patent is hereby corrected as shown below:

In the Claims

In Column 16, Line 1, Claim 16, after "and a polarization" insert -- state --.

Signed and Sealed this
Twelfth Day of February, 2019

Andrei Iancu
*Director of the United States Patent and Trademark Office*